US012426912B2

(12) United States Patent
Zhao et al.

(10) Patent No.: US 12,426,912 B2
(45) Date of Patent: Sep. 30, 2025

(54) SURGICAL INSTRUMENTS, SYSTEMS, AND METHODS FOR FREQUENCY DITHERING CONTROL FUNCTIONALITY (71) Applicant: Covidien LP, Mansfield, MA (US)

(72) Inventors: Jing Zhao, Superior, CO (US); David J. Van Tol, Boulder, CO (US); Keith W. Malang, Longmont, CO (US); Matthew S. Cowley, Frederick, CO (US)

(73) Assignee: Covidien LP, Mansfield, MA (US)

( * ) Notice: Subject to any disclaimer, the term of this patent is extended or adjusted under 35 U.S.C. 154(b) by 814 days.

(21) Appl. No.: 17/710,217

(22) Filed: Mar. 31, 2022

(65) Prior Publication Data

US 2022/0401121 A1 Dec. 22, 2022

Related U.S. Application Data

(60) Provisional application No. 63/211,614, filed on Jun. 17, 2021.

(51) Int. Cl.
*A61B 17/32* (2006.01)
*A61B 17/00* (2006.01)

(52) U.S. Cl.
CPC .......... *A61B 17/320092* (2013.01); *A61B 2017/00075* (2013.01); *A61B 2017/320074* (2017.08); *A61B 2017/320093* (2017.08)

(58) Field of Classification Search
CPC A61B 17/320068; A61B 2017/320093; A61B 17/22004; A61B 17/22029; A61B 2017/320094; A61B 2017/22014; A61B 2017/00075; A61B 2017/22005; A61B 2017/22011; A61B 2017/22012; A61B 2017/22015; A61B 2017/320069; A61B 2017/320071; A61B 2017/320073; A61B 2017/320074; A61B 2017/320082; A61B 2017/320089; A61B 2017/320095; A61B 2018/00994; A61N 7/02

See application file for complete search history.

(56) References Cited

U.S. PATENT DOCUMENTS

| 1,813,902 A | 7/1931 | Bovie |
| 2,874,470 A | 2/1959 | Richards |
| 2,990,616 A | 7/1961 | Balamuth |
| 3,432,691 A | 3/1969 | Shoh |

(Continued)

*Primary Examiner* — Joseph A Stoklosa
*Assistant Examiner* — Marina Delaney Templeton (57) ABSTRACT

An ultrasonic surgical system includes an ultrasonic generator configured to provide an ultrasonic drive signal, and an ultrasonic transducer electrically coupled to the ultrasonic generator to receive the ultrasonic drive signal therefrom and configured, in response to the received ultrasonic drive signal, to produce a mechanical motion. The ultrasonic surgical system further includes a sensor configured to sense a frequency and a magnitude of the mechanical motion, and a controller configured to receive a target mechanical motion to be produced by the ultrasonic transducer and control the ultrasonic drive signal so that a frequency of the ultrasonic drive signal falls within a frequency range around a resonant frequency of the ultrasonic transducer, the frequency range corresponding to the target mechanical motion produced by the ultrasonic transducer.

16 Claims, 8 Drawing Sheets

(56) References Cited

U.S. PATENT DOCUMENTS

| | | |
|---|---|---|
| 3,489,930 A | 1/1970 | Shoh |
| 3,526,792 A | 9/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,309,067 A | 1/1982 | Riley, Jr. |
| 4,370,302 A | 1/1983 | Suzuoka et al. |
| 4,641,053 A | 2/1987 | Takeda |
| 4,903,696 A | 2/1990 | Stasz et al. |
| 5,113,116 A | 5/1992 | Wilson |
| 5,224,680 A | 7/1993 | Greenstein et al. |
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,553,478 A | 9/1996 | Di Troia |
| 5,565,520 A | 10/1996 | Fock et al. |
| 5,582,617 A | 12/1996 | Klieman et al. |
| 5,593,414 A | 1/1997 | Shipp et al. |
| 5,600,230 A | 2/1997 | Dunstan |
| 5,685,311 A | 11/1997 | Hara |
| 5,717,306 A | 2/1998 | Shipp |
| 5,728,130 A | 3/1998 | Ishikawa et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,949,213 A | 9/1999 | Lanni |
| 5,954,736 A | 9/1999 | Bishop et al. |
| 5,993,465 A | 11/1999 | Shipp et al. |
| 5,994,855 A | 11/1999 | Lundell et al. |
| 6,028,387 A | 2/2000 | Boukhny |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,162,194 A | 12/2000 | Shipp |
| 6,183,426 B1 | 2/2001 | Akisada et al. |
| 6,220,098 B1 | 4/2001 | Johnson et al. |
| 6,220,368 B1 | 4/2001 | Ark et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,346,795 B2 | 2/2002 | Haraguchi et al. |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,977,587 B2 | 7/2011 | Rajagopal et al. |
| 9,017,355 B2 | 4/2015 | Smith et al. |
| 9,107,690 B2 | 8/2015 | Bales, Jr. et al. |
| 9,314,261 B2 | 4/2016 | Bales, Jr. et al. |
| 10,194,972 B2 | 2/2019 | Yates et al. |
| 10,194,973 B2 | 2/2019 | Wiener et al. |
| 10,265,117 B2 | 4/2019 | Wiener et al. |
| 10,321,950 B2 | 6/2019 | Yates et al. |
| 10,335,614 B2 | 7/2019 | Messerly et al. |
| 10,342,602 B2 | 7/2019 | Strobl et al. |
| 10,368,894 B2 | 8/2019 | Madan et al. |
| 10,376,305 B2 | 8/2019 | Yates et al. |
| 10,420,579 B2 | 9/2019 | Wiener et al. |
| 10,537,394 B2 | 1/2020 | Strobl |
| 10,537,399 B2 | 1/2020 | Eckert et al. |
| 10,624,667 B2 | 4/2020 | Faller et al. |
| 10,639,059 B2 | 5/2020 | Groene et al. |
| 10,653,437 B2 | 5/2020 | Dannaher et al. |
| 10,687,884 B2 | 6/2020 | Wiener et al. |
| 10,736,685 B2 | 8/2020 | Wiener et al. |
| 10,751,108 B2 | 8/2020 | Yates et al. |
| 10,799,913 B2 | 10/2020 | Bales, Jr. et al. |
| 10,813,703 B2 | 10/2020 | Swayze et al. |
| 10,898,256 B2 | 1/2021 | Yates et al. |
| 10,912,580 B2 | 2/2021 | Green et al. |
| 10,952,788 B2 | 3/2021 | Asher et al. |
| 11,033,292 B2 | 6/2021 | Green et al. |

(56) References Cited

U.S. PATENT DOCUMENTS

| | | |
|---|---|---|
| 11,058,475 B2 | 7/2021 | Wiener et al. |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2002/0138090 A1 | 9/2002 | Jewett |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0033201 A1 | 2/2005 | Takahashi et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0159752 A1 | 7/2005 | Walker et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0076934 A1 | 4/2006 | Ogata et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2006/0220613 A1 | 10/2006 | Abe |
| 2007/0011836 A1 | 1/2007 | Brewer et al. |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0227866 A1 | 10/2007 | Dimig |
| 2007/0239028 A1 | 10/2007 | Houser et al. |
| 2007/0239101 A1 | 10/2007 | Kellogg |
| 2008/0033248 A1 | 2/2008 | Akagi |
| 2008/0051693 A1 | 2/2008 | Babaev |
| 2008/0215056 A1 | 9/2008 | Miller et al. |
| 2008/0245841 A1 | 10/2008 | Smith et al. |
| 2008/0251568 A1 | 10/2008 | Zemlok et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0000074 A1 | 1/2010 | Smith et al. |
| 2010/0004669 A1 | 1/2010 | Smith et al. |
| 2011/0009890 A1 | 1/2011 | Palmer et al. |
| 2011/0024479 A1 | 2/2011 | Swensgard et al. |
| 2011/0087256 A1 | 4/2011 | Wiener et al. |
| 2012/0078278 A1 | 3/2012 | Bales, Jr. et al. |
| 2013/0267975 A1 | 10/2013 | Timm et al. |
| 2013/0282003 A1 | 10/2013 | Messerly |
| 2013/0331873 A1* | 12/2013 | Ross .................... B06B 1/0207 606/169 |
| 2014/0288465 A1* | 9/2014 | Akagane ........ A61B 17/320068 601/2 |
| 2015/0105768 A1* | 4/2015 | Gilbert .............. A61B 18/1206 606/34 |
| 2015/0157354 A1 | 6/2015 | Bales, Jr. |
| 2017/0332909 A1 | 11/2017 | Nagae |
| 2018/0042659 A1* | 2/2018 | Rupp ...................... A61N 7/00 |

* cited by examiner

FIG. 9

SURGICAL INSTRUMENTS, SYSTEMS, AND METHODS FOR FREQUENCY DITHERING CONTROL FUNCTIONALITY

CROSS-REFERENCE TO RELATED APPLICATIONS

This application claims the benefit of, and priority to, U.S. Provisional Patent Application No. 63/211,614, filed on Jun. 17, 2021, the entire contents of which are hereby incorporated herein by reference.

FIELD

The present disclosure relates to energy-based surgical instruments and, more particularly, to ultrasonic surgical instruments, systems, and methods incorporating dithering control functionality for treating tissue.

BACKGROUND

Ultrasonic surgical instruments and systems utilize ultrasonic energy, i.e., ultrasonic vibrations, to treat tissue. More specifically, ultrasonic surgical instruments and systems utilize mechanical vibration energy transmitted at ultrasonic frequencies to treat tissue. An ultrasonic surgical device may include, for example, an ultrasonic blade and a clamp mechanism to enable clamping of tissue against the blade. Ultrasonic energy transmitted to the blade causes the blade to vibrate at very high frequencies, which allows for heating tissue to treat tissue clamped against or otherwise in contact with the blade.

SUMMARY

As used herein, the term "distal" refers to the portion that is described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is an ultrasonic surgical system, which includes an ultrasonic generator configured to provide an ultrasonic drive signal, and an ultrasonic transducer electrically coupled to the ultrasonic generator to receive the ultrasonic drive signal therefrom and configured, in response to the received ultrasonic drive signal, to produce a mechanical motion. The ultrasonic surgical system further includes a sensor configured to sense a frequency and a magnitude of the mechanical motion, and a controller configured to receive a target mechanical motion to be produced by the ultrasonic transducer and control the ultrasonic drive signal so that a frequency of the ultrasonic drive signal falls within a frequency range around a resonant frequency of the ultrasonic transducer, the frequency range corresponding to the target mechanical motion produced by the ultrasonic transducer.

In an aspect of the present disclosure, the controller is further configured to provide a test signal to the ultrasonic transducer. The test signal is an impulse signal.

In another aspect of the present disclosure, the controller is further configured to analyze an impulse response from the ultrasonic transducer in response to the test signal. The resonant frequency of the ultrasonic transducer is calculated based on the impulse response.

In yet another aspect of the present disclosure, the controller is further configured to increase the frequency range of the ultrasonic drive signal when the mechanical motion is greater than the target mechanical motion.

In still another aspect of the present disclosure, the controller is further configured to maintain the frequency range of the ultrasonic drive signal when the mechanical motion is equal to the target motion.

In another aspect of the present disclosure, the controller is further configured to decrease the frequency range of the ultrasonic drive signal when the mechanical motion is less than the target mechanical motion.

In still yet another aspect of the present disclosure, the sensor is a mechanical bridge.

In still another aspect of the present disclosure, an upper bound and a lower bound of the frequency range are −3 dB points with respect to the resonant frequency.

A method for controlling ultrasonic drive signal to produce mechanical ultrasonic energy provided in accordance with aspects of the present disclosure includes providing, by an ultrasonic generator, an ultrasonic drive signal to an ultrasonic transducer, in response to the received ultrasonic drive signal, producing a mechanical motion by the ultrasonic transducer, sensing a frequency and a magnitude of the mechanical motion, receiving a target mechanical motion to be produced by the ultrasonic transducer; and controlling the ultrasonic drive signal so that a frequency of the ultrasonic drive signal falls within a frequency range around a resonant frequency of the ultrasonic transducer, the frequency range corresponding to the target mechanical motion produced by the ultrasonic transducer.

In an aspect of the present disclosure, the method further includes providing a test signal to the ultrasonic transducer. The test signal is an impulse signal.

In another aspect of the present disclosure, the method further includes analyzing an impulse response from the ultrasonic transducer in response to the test signal. The resonant frequency of the ultrasonic transducer is calculated based on the impulse response.

In yet another aspect of the present disclosure, controlling the ultrasonic drive signal includes increasing the frequency range of the ultrasonic drive signal when the mechanical motion is greater than the target mechanical motion.

In still another aspect of the present disclosure, controlling the ultrasonic drive signal includes maintaining the frequency range of the ultrasonic drive signal when the mechanical motion is equal to the target motion.

In another aspect of the present disclosure, controlling the ultrasonic drive signal includes decreasing the frequency range of the ultrasonic drive signal when the mechanical motion is less than the target mechanical motion.

In still yet another aspect of the present disclosure, controlling the ultrasonic drive signal includes regulating a phase different between the ultrasonic drive signal and a motional feedback signal to be within a predetermined phase range.

A nontransitory computer-readable medium including processor-executable instructions is provided in accordance with aspects of the present disclosure. The instructions, when executed by a processor, cause the computer to perform a method for controlling ultrasonic drive signal to produce mechanical ultrasonic energy. The method includes providing, by an ultrasonic generator, an ultrasonic drive signal to an ultrasonic transducer, in response to the received ultrasonic drive signal, producing a mechanical motion by the ultrasonic transducer, sensing a frequency and a magnitude of the mechanical motion, receiving a target mechanical motion to be produced by the ultrasonic transducer; and controlling the ultrasonic drive signal so that a frequency of the ultrasonic drive signal falls within a frequency range around a resonant frequency of the ultrasonic transducer, the frequency range corresponding to the target mechanical motion produced by the ultrasonic transducer.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1:
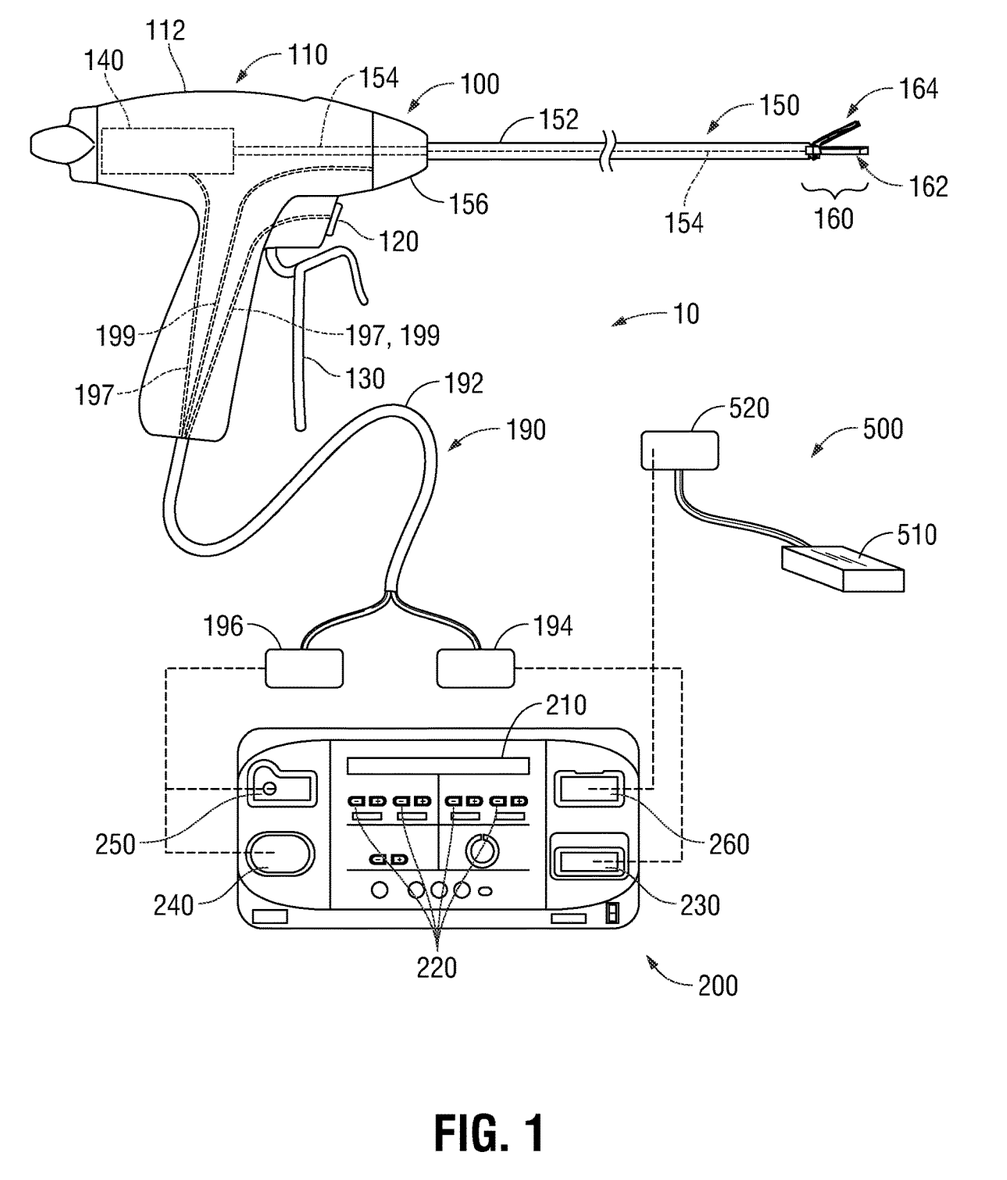
FIG. 1 is a side view of a surgical system provided in accordance with the present disclosure including a surgical instrument, a surgical generator, and a return electrode device.

Referring to FIG. 1, a surgical system provided in accordance with aspects of the present disclosure is shown generally identified by reference numeral 10 including a surgical instrument 100 and a surgical generator 200. Surgical instrument 100 includes a handle assembly 110, an elongated assembly 150 extending distally from handle assembly 110, an end effector assembly 160 disposed at a distal end of elongated assembly 150, and a cable assembly 190 operably coupled with handle assembly 110 and extending therefrom for connection to surgical generator 200.

Surgical generator 200 includes a display 210, a plurality user interface features 220 (e.g., buttons, knobs, touch screens, switches, etc.), an ultrasonic plug port 230, and an electrosurgical plug port 240. Display 210 is configured to display operating parameters, settings, etc. during use and, in aspects, may be configured as a touch-screen display configured to enable input by a user. User interface features 220 enable input by a user such as, for example, to power on surgical generator 200, initiate energy delivery, change settings, manipulate the information shown on display 210, etc. Ports 230, 240 enable connection of surgical generator 200 with surgical instrument 100 for output of ultrasonic and electrosurgical energy, respectively, thereto. Additional ports for other energy outputs, fluid supply (irrigation and/or aspiration), smoke evacuation, etc. are also contemplated. Further, as an alternative to plural dedicated ports (e.g., ports 230, 240), one or more common ports (not shown) may be provided.

Surgical instrument 100 may be configured to operate in an electrosurgical mode supplying Radio Frequency (RF) energy to tissue to treat tissue and/or in an ultrasonic mode supplying ultrasonic energy to tissue to treat tissue. The electrosurgical and ultrasonic modes, where both are provided, may operate consecutively, simultaneously, in overlapping or nested temporal relation, and/or in any other suitable configuration. The mode(s) activated; the type of activation(s), e.g., continuous, intermittent, periodic, etc.; and/or the energy level setting, e.g., LOW or sealing power ultrasonic, HIGH or transecting power ultrasonic, sealing RF energy, transecting RF energy, coagulating RF energy, etc., may depend upon a user intent (e.g., sealing vs. transection), a type of tissue, a size (e.g., diameter) of tissue, and/or other factors. Surgical generator 200 is a combined ultrasonic generator and electrosurgical generator, although separate ultrasonic and electrosurgical generators are also contemplated. Surgical generator 200, more specifically, is configured to produce ultrasonic drive signals for output through ultrasonic plug port 230 to surgical instrument 100 to activate surgical instrument 100 in the ultrasonic mode (and to control the ultrasonic mode in accordance with the appropriate energy settings) and to provide electrosurgical energy for output through electrosurgical plug port 240 to activate surgical instrument 100 in the electrosurgical mode (and to control the electrosurgical mode in accordance with the appropriate energy settings).

Surgical generator 200 may generate and provide a test or ping signal to surgical instrument 100 and analyze a response signal from surgical instrument 100. The ping signal may be an impulse signal and the response signal may be an impulse response. The ping signal may be provided to surgical instrument 100 periodically, sporadically, automatically, or when requested before or during surgical operations. The impulse response can be analyzed to identify characteristics of surgical instrument 100, such as a resonant frequency, a level of mechanical wear, a damping ratio (1/Q, where Q is the quality factor; this can be used, for example, to determine the lower and upper bounds of the frequency passband), and/or a system ID of surgical instrument 100.

Continuing with reference to FIG. 1, handle assembly 110 includes a housing 112, an activation button 120, and a clamp trigger 130. Housing 112 is configured to support an ultrasonic transducer 140. Ultrasonic transducer 140 may be permanently engaged within housing 112 or removable therefrom. Ultrasonic transducer 140 includes a piezoelectric stack other suitable ultrasonic transducer components electrically coupled to surgical generator 200, e.g., via one or more of first electrical lead wires 197, to enable communication of ultrasonic drive signals to ultrasonic transducer 140 to drive ultrasonic transducer 140 to produce ultrasonic vibration energy that is transmitted along a waveguide 154 of elongated assembly 150 to blade 162 of end effector assembly 160 of elongated assembly 150, as detailed below. Feedback and/or control signals, e.g., including the test or ping signals, may likewise be communicated between ultrasonic transducer 140 and surgical generator 200. Ultrasonic transducer 140, more specifically, may include a stack of piezoelectric elements secured, under pre-compression between proximal and distal end masses or a proximal end mass and an ultrasonic horn with first and second electrodes electrically coupled between piezoelectric elements of the stack of piezoelectric elements to enable energization thereof to produce ultrasonic energy. However, other suitable ultrasonic transducer configurations, including plural transducers and/or non-longitudinal, e.g., torsional, transducers are also contemplated.

When the test or ping signal is provided to ultrasonic transducer 140, the resonant frequency thereof may be identified and used in controlling ultrasonic transducer 140, as detailed below.

An activation button 120 is disposed on housing 112 and coupled to or between ultrasonic transducer 140 and/or surgical generator 200, e.g., via one or more of first electrical lead wires 197, to enable activation of ultrasonic transducer 140 in response to depression of activation button 120. In some configurations, activation button 120 may include an ON/OFF switch. In other configurations, activation button 120 may include multiple actuation switches to enable activation from an OFF position to different actuated positions corresponding to different activation settings, e.g., a first actuated position corresponding to a first activation setting (such as a LOW power or tissue sealing setting) and a second actuated position corresponding to a second activation setting (such as a HIGH power or tissue transection setting). In still other configurations, separate activation buttons may be provided, e.g., a first actuation button for activating a first activation setting and a second activation button for activating a second activation setting. Additional activation buttons, sliders, wheels, etc. are also contemplated to enable control of various different activation settings from housing 112.

Elongated assembly 150 of surgical instrument 100 includes an outer drive sleeve 152, an inner support sleeve 153 (FIG. 4) disposed within outer drive sleeve 152, a waveguide 154 extending through inner support sleeve 153 (FIG. 4), a drive assembly (not shown), a rotation knob 156, and an end effector assembly 160 including a blade 162 and a jaw member 164. Rotation knob 156 is rotatable in either direction to rotate elongated assembly 150 in either direction relative to handle assembly 110. The drive assembly operably couples a proximal portion of outer drive sleeve 152 to clamp trigger 130 of handle assembly 110. A distal portion of outer drive sleeve 152 is operably coupled to jaw member 164 and a distal end of inner support sleeve 153 (FIG. 4) pivotably supports jaw member 164. As such, clamp trigger 130 is selectively actuatable to thereby move outer drive sleeve 152 about inner support sleeve 153 (FIG. 4) to pivot jaw member 164 relative to blade 162 of end effector assembly 160 from a spaced apart position to an approximated position for clamping tissue between jaw member 164 and blade 162. The configuration of outer and inner sleeves 152, 153 (FIG. 4) may be reversed, e.g., wherein outer sleeve 152 is the support sleeve and inner sleeve 153 (FIG. 4) is the drive sleeve. Other suitable drive structures as opposed to a sleeve are also contemplated such as, for example, drive rods, drive cables, drive screws, etc.

Referring still to FIG. 1, the drive assembly may be tuned to provide a jaw clamping force, or jaw clamping force within a jaw clamping force range, to tissue clamped between jaw member 164 and blade 162 or may include a force limiting feature whereby the clamping force applied to tissue clamped between jaw member 164 and blade 162 is limited to a particular jaw clamping force or a jaw clamping force within a jaw clamping force range.

Figure 4:
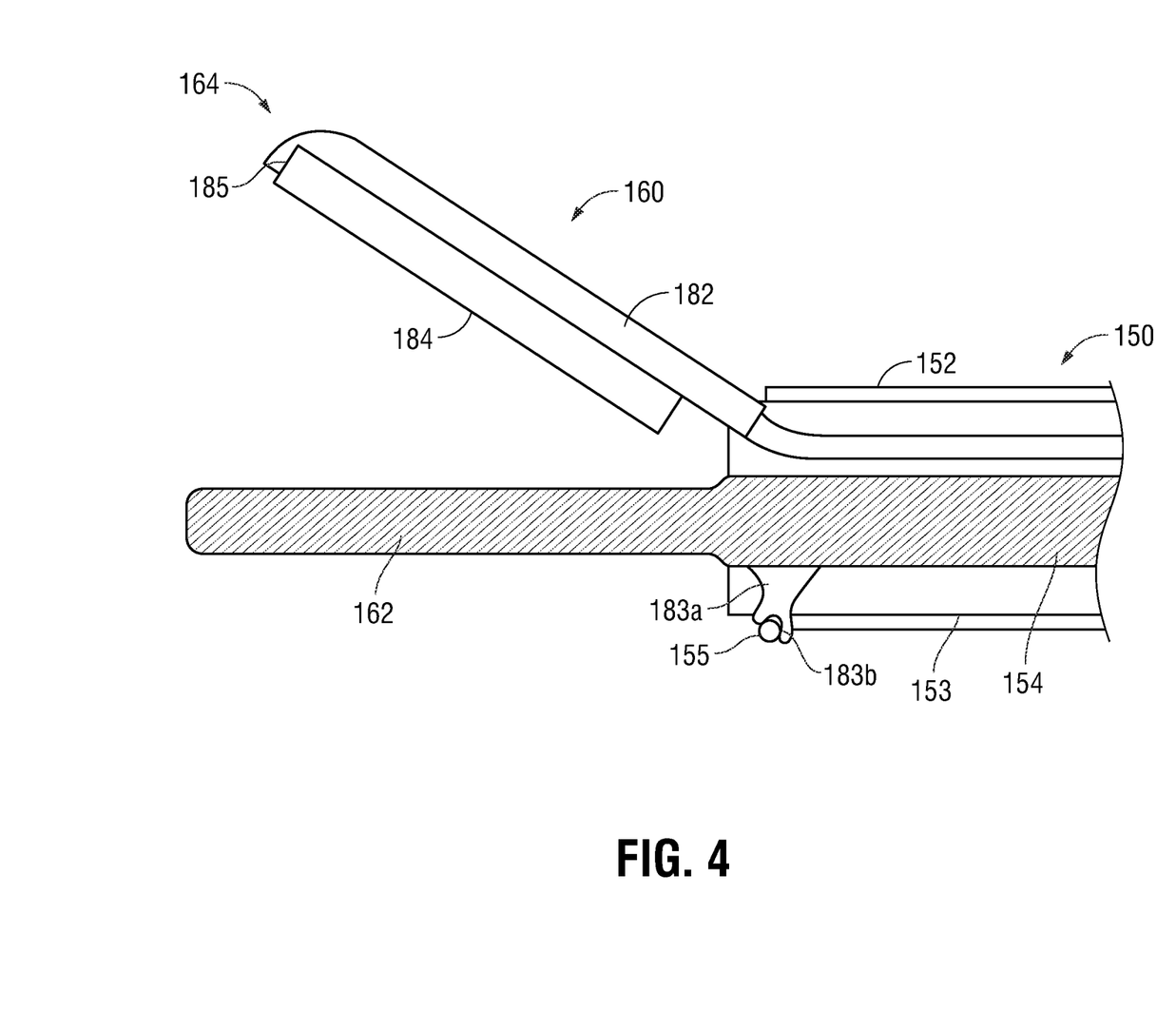
FIG. 4 is a longitudinal, cross-sectional view of an end effector assembly of the surgical instrument of FIG. 1.

Waveguide 154, as noted above, extends from handle assembly 110 through inner sleeve 153 (FIG. 4). Waveguide 154 includes blade 162 disposed at a distal end thereof. Blade 162 may be integrally formed with waveguide 154, separately formed and subsequently attached (permanently or removably) to waveguide 154, or otherwise operably coupled with waveguide 154. Waveguide 154 and/or blade 162 may be formed from titanium, a titanium alloy, or other suitable electrically conductive material(s), although non-conductive materials are also contemplated. Waveguide 154 includes a proximal connector (not shown), e.g., a threaded male connector, configured for engagement, e.g., threaded engagement within a threaded female receiver, of ultrasonic transducer 140 such that ultrasonic motion produced by ultrasonic transducer 140 is transmitted along waveguide 154 to blade 162 for treating tissue clamped between blade 162 and jaw member 164 or positioned adjacent to blade 162.

Cable assembly 190 of surgical instrument 100 includes a cable 192, an ultrasonic plug 194, and an electrosurgical plug 196. Ultrasonic plug 194 is configured for connection with ultrasonic plug port 230 of surgical generator 200 while electrosurgical plug 196 is configured for connection with bipolar electrosurgical plug port 240 of surgical generator 200 and/or active monopolar electrosurgical plug port 250 of surgical generator 200. In configurations where generator 200 includes a common port, cable assembly 190 may include a common plug (not shown) configured to act as both the ultrasonic plug 194 and the electrosurgical plug 196. In configurations where surgical instrument 100 is only configured for ultrasonic operation, electrosurgical plug 196 and associated components are omitted.

Plural first electrical lead wires 197 electrically coupled to ultrasonic plug 194 extend through cable 192 and into handle assembly 110 for electrical connection to ultrasonic transducer 140 and/or activation button 120 to enable the selective supply of ultrasonic drive signals from surgical generator 200 to ultrasonic transducer 140 upon activation of activation button 120 in an ultrasonic mode. In addition, plural second electrical lead wires 199 are electrically coupled to electrosurgical plug 196 and extend through cable 192 into handle assembly 110. In bipolar configurations, separate second electrical lead wires 199 are electrically coupled to waveguide 154 and jaw member 164 (and/or different portions of jaw member 164) such that bipolar electrosurgical energy may be conducted between blade 162 and jaw member 164 (and/or between different portions of jaw member 164). In monopolar configurations, a second electrical lead wire 199 is electrically coupled to waveguide 154 such that monopolar electrosurgical energy may be supplied to tissue from blade 162. Alternatively or additionally, a second electrical lead wire 199 may electrically couple to jaw member 164 in the monopolar configuration to enable monopolar electrosurgical energy to be supplied to tissue from jaw member 164. In configurations where both bipolar and monopolar functionality are enabled, one or more of the second electrical lead wires 199 may be used for both the delivery of bipolar energy and monopolar energy; alternatively, bipolar and monopolar energy delivery may be provided by separate second electrical lead wires 199. One or more other second electrical lead wires 199 is electrically coupled to activation button 120 to enable the selective supply of electrosurgical energy from surgical generator 200 to waveguide 154 and/or jaw member 164 upon activation of activation button 120 in an electrosurgical mode(s). Further, second electrical lead wire 199 may be used to supply a test or ping signal (e.g., an impulse, sinusoid, saw-tooth, step, or other signal) to obtain the impulse response from ultrasonic transducer 140 so that the identification or characteristics (e.g., a resonant frequency) of ultrasonic transducer 140 can be identified or obtained based on the impulse response.

As an alternative to a remote generator 200, surgical system 10 may be at least partially cordless in that it incorporates an ultrasonic generator, an electrosurgical generator, and/or a power source, e.g., a battery, thereon or therein. In this manner, the connections from surgical instrument 100 to external devices, e.g., generator(s) and/or power source(s), is reduced or eliminated. More specifically, with reference to FIG. 2, another surgical system in accordance with the present disclosure is shown illustrated as a surgical instrument 20 supporting an ultrasonic generator 310, a power source (e.g., battery assembly 400), and an electrosurgical generator 600 thereon or therein. Surgical instrument 20 is similar to surgical instrument 100 (FIG. 1) and may include any of the features thereof except as explicitly contradicted below. Accordingly, only differences between surgical instrument 20 and surgical instrument 100 (FIG. 1) are described in detail below while similarities are omitted or summarily described.

Figure 2:
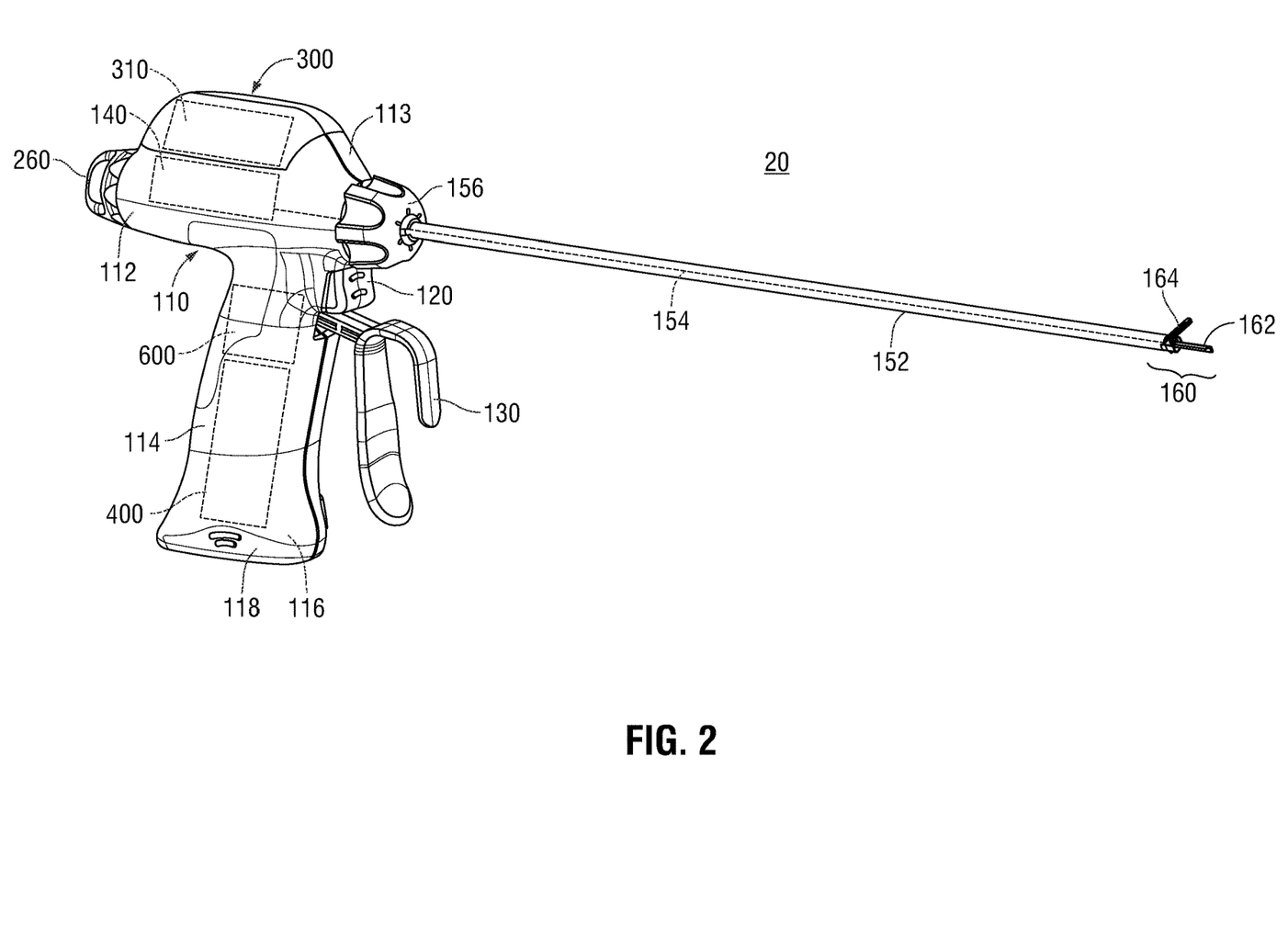
FIG. 2 is perspective view of another surgical system provided in accordance with the present disclosure including a surgical instrument incorporating an ultrasonic generator, electrosurgical generator, and power source therein.

Housing 112 of surgical instrument 20 includes a body portion 113 and a fixed handle portion 114 depending from body portion 113. Body portion 113 of housing 112 is configured to support an ultrasonic transducer and generator assembly ("TAG") 300 including ultrasonic generator 310 and ultrasonic transducer 140. TAG 300 may be permanently engaged with body portion 113 of housing 112 or removable therefrom.

Fixed handle portion 114 of housing 112 defines a compartment 116 configured to receive battery assembly 400 and electrosurgical generator 600 and a door 118 configured to enclose compartment 116. An electrical connection assembly (not shown) is disposed within housing 112 and serves to electrically couple activation button 120, ultrasonic generator 310 of TAG 300, and battery assembly 400 with one another when TAG 300 is supported on or in body portion 113 of housing 112 and battery assembly 400 is disposed within compartment 116 of fixed handle portion 114 of housing 112, thus enabling activation of surgical instrument 20 in an ultrasonic mode in response to appropriate actuation of activation button 120. Further, the electrical connection assembly or a different electrical connection assembly disposed within housing 112 serves to electrically couple activation button 120, electrosurgical generator 600, battery assembly 400, and end effector assembly 160 (e.g., blade 162 and jaw member 164 and/or different portions of jaw member 164) with one another when electrosurgical generator 600 and battery assembly 400 are disposed within compartment 116 of fixed handle portion 114 of housing 112, thus enabling activation of surgical instrument 20 in an electrosurgical mode, e.g., bipolar RF, in response to appropriate actuation of activation button 120. For a monopolar electrosurgical mode, return electrode device 500 (FIG. 1) may be configured to connect to surgical instrument 20 (electrosurgical generator 600 thereof, more specifically), to complete a monopolar circuit through tissue and between surgical instrument 20 (e.g., blade 162 and/or jaw member 164) and return electrode device 500 (FIG. 1).

Figure 3:
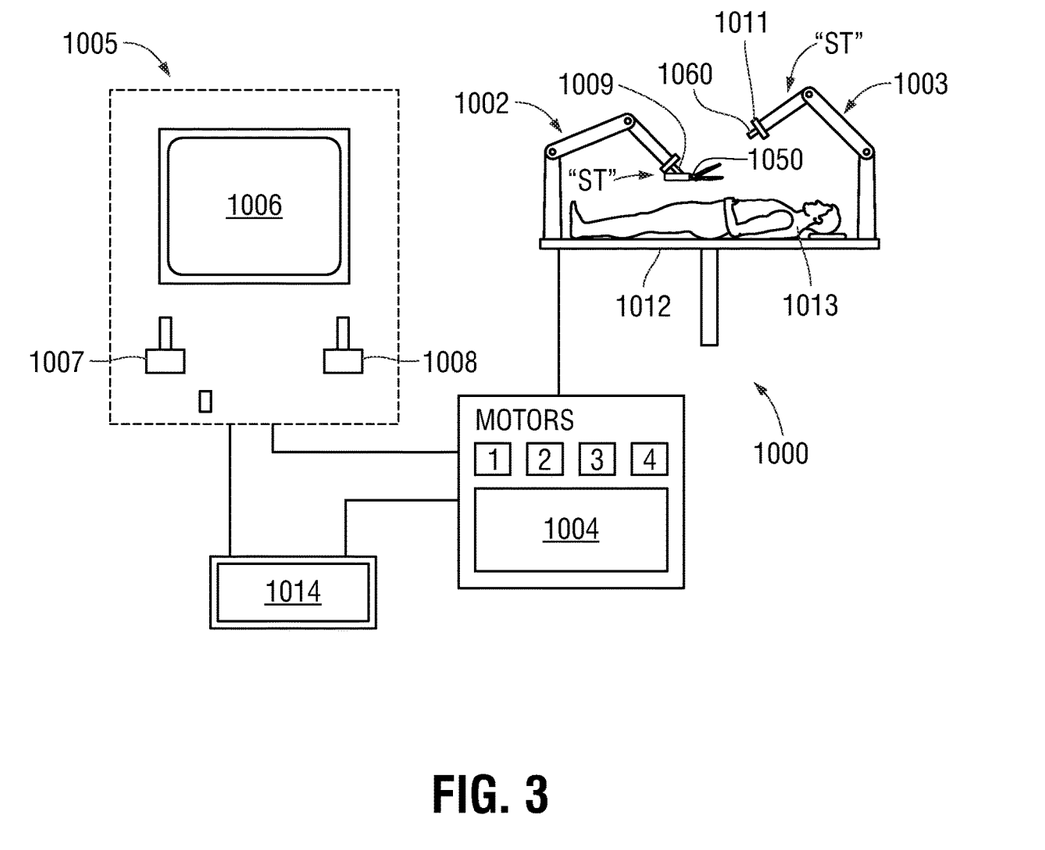
FIG. 3 is a schematic illustration of a robotic surgical system provided in accordance with the present disclosure.

Turning to FIG. 3, a robotic surgical system in accordance with the aspects and features of the present disclosure is shown generally identified by reference numeral 1000. For the purposes herein, robotic surgical system 1000 is generally described. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three dimensional images; and manual input devices 1007, 1008, by means of which a person (not shown), for example a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, a surgical tool "ST" supporting an end effector 1050, 1060. One of the surgical tools "ST" may be surgical instrument 100 (FIG. 1), surgical instrument 20 (FIG. 2), or any other suitable surgical instrument 20 configured for use in both an ultrasonic mode and one or more electrosurgical (bipolar and/or monopolar) modes, wherein manual actuation features, e.g., actuation button 120 (FIG. 1), clamp lever 130 (FIG. 1), etc., are replaced with robotic inputs. In such configurations, robotic surgical system 1000 may include or be configured to connect to an ultrasonic generator, an electrosurgical generator, and/or a power source. The other surgical tool "ST" may include any other suitable surgical instrument, e.g., an endoscopic camera, other surgical tool, etc. Robot arms 1002, 1003 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and, thus, the surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 5:
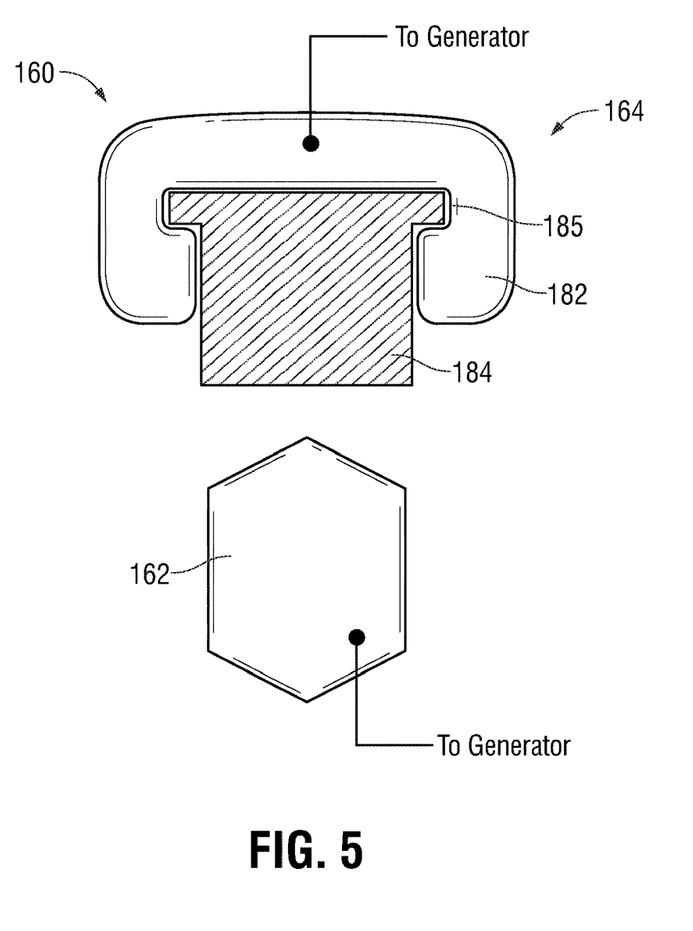
FIG. 5 is a transverse, cross-sectional view of the end effector assembly of FIG. 4.
Figure 6:
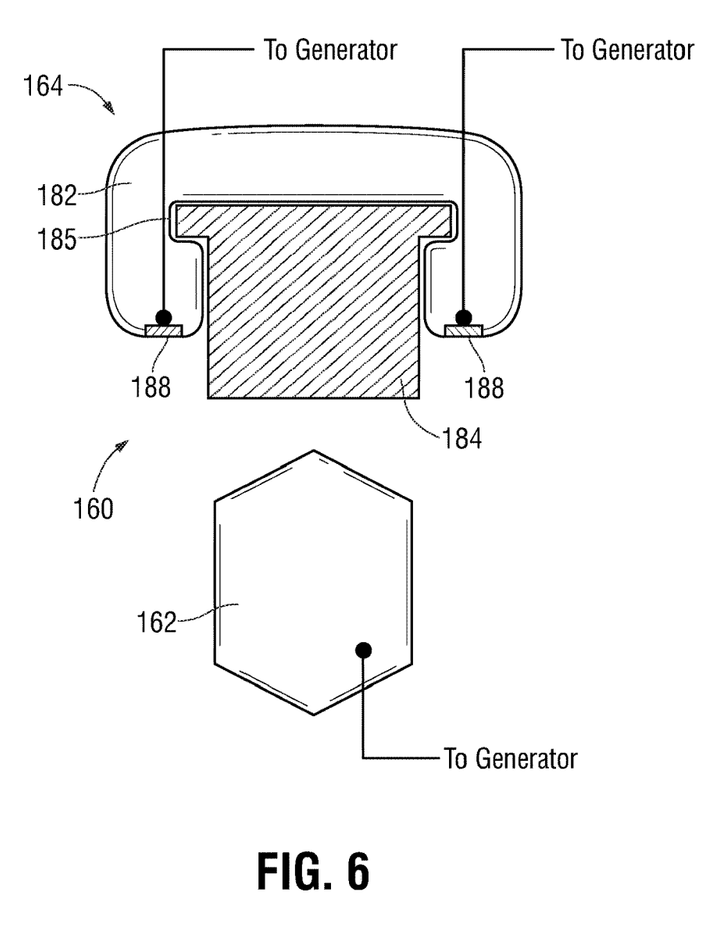
FIG. 6 is a transverse, cross-sectional view of another configuration of the end effector assembly of FIG. 4.

Referring to FIGS. 4-6, end effector assembly 160 of surgical instrument 100 of surgical system 10 (FIG. 1) is detailed, although the aspects and features of end effector assembly 160 may similarly apply, to the extent consistent, to surgical instrument 20 (FIG. 2) and/or any other suitable surgical instrument or system. End effector assembly 160, as noted above, includes blade 162 and jaw member 164. Blade 162 may define a linear configuration, may define a curved configuration, or may define any other suitable configuration, e.g., straight and/or curved surfaces, portions, and/or sections; one or more convex and/or concave surfaces, portions, and/or sections; etc. With respect to curved configurations, blade 162, more specifically, may be curved in any direction relative to jaw member 164, for example, such that the distal tip of blade 162 is curved towards jaw member 164, away from jaw member 164, or laterally (in either direction) relative to jaw member 164. Further, blade 162 may be formed to include multiple curves in similar directions, multiple curves in different directions within a single plane, and/or multiple curves in different directions in different planes. In addition, blade 162 may additionally or alternatively be formed to include any suitable features, e.g., a tapered configuration, various different cross-sectional configurations along its length, cut outs, indents, edges, protrusions, straight surfaces, curved surfaces, angled surfaces, wide edges, narrow edges, and/or other features.

Blade 162 may define a polygonal, rounded polygonal, or any other suitable cross-sectional configuration(s). Waveguide 154 or at least the portion of waveguide 154 proximally adjacent blade 162, may define a cylindrical shaped configuration. Plural tapered surfaces (not shown) may interconnect the cylindrically shaped waveguide 154 with the polygonal (rounded edge polygonal, or other suitable shape) configuration of blade 162 to define smooth transitions between the body of waveguide 154 and blade 162.

Blade 162 may be wholly or selectively coated with a suitable material, e.g., a non-stick material, an electrically insulative material, an electrically conductive material, combinations thereof, etc. Suitable coatings and/or methods of applying coatings include but are not limited to Teflon®, polyphenylene oxide (PPO), deposited liquid ceramic insulative coatings; thermally sprayed coatings, e.g., thermally sprayed ceramic; Plasma Electrolytic Oxidation (PEO) coatings; anodization coatings; sputtered coatings, e.g., silica; ElectroBond® coating available from Surface Solutions Group of Chicago, IL, USA; or other suitable coatings and/or methods of applying coatings.

Continuing with reference to FIGS. 4-6, blade 162, as noted above, in addition to receiving ultrasonic energy transmitted along waveguide 154 from ultrasonic transducer 140 (FIG. 1), may also be adapted to connect to generator 200 (FIG. 1) to enable the supply of RF energy to blade 162 for conduction to tissue in contact therewith. In bipolar configurations, RF energy is conducted between blade 162 and jaw member 164 (or between portions of jaw member 164 and/or blade 162) and through tissue disposed therebetween to treat tissue. In monopolar configurations, RF energy is conducted from blade 162, serving as the active electrode, to tissue in contact therewith and is ultimately returned to generator 200 (FIG. 1) via return electrode device 500 (FIG. 1), serving as the passive or return electrode.

Jaw member 164 of end effector assembly 160 includes more rigid structural body 182 and more compliant jaw liner 184. Structural body 182 may be formed from an electrically conductive material, e.g., stainless steel, and/or may include electrically conductive portions. Structural body 182 includes a pair of proximal flanges 183a that are pivotably coupled to the inner support sleeve 153 via receipt of pivot bosses (not shown) of proximal flanges 183a within corresponding openings (not shown) defined within the inner support sleeve 153 and operably coupled with outer drive sleeve 152 via a drive pin 155 secured relative to outer drive sleeve 152 and pivotably received within apertures 183b defined within proximal flanges 183a. As such, sliding of outer drive sleeve 152 about inner support sleeve 153 pivots jaw member 164 relative to blade 162 from a spaced apart position to an approximated position to clamp tissue between jaw liner 184 of jaw member 164 and blade 162.

With reference to FIG. 5, structural body 182 may be adapted to connect to a source of electrosurgical energy, e.g., generator 200 (FIG. 1), and, in a bipolar electrosurgical mode, is charged to a different potential as compared to blade 162 to enable the conduction of bipolar electrosurgical (e.g., RF) energy through tissue clamped therebetween, to treat the tissue. In a monopolar electrosurgical mode, structural body 182 may be un-energized, may be charged to the same potential as compared to blade 162 (thus both defining the active electrode), or may be energized while blade 162 is not energized (wherein structural body 182 defines the active electrode). In either monopolar configuration, energy is returned to generator 200 (FIG. 1) via return electrode device 500 (FIG. 1), which serves as the passive or return electrode.

Referring to FIG. 6, as an alternative to the entirety of structural body 182 of jaw member 164 being connected to generator 200 (FIG. 1), the structural body may be formed from or embedded at least partially in an insulative material, e.g., an overmolded plastic. In such configurations, electrically conductive surfaces 188, e.g., in the form of plates, may be disposed on (e.g., bonded to, deposited onto, mechanically engaged with, etc.) or captured by the insulative material (e.g., overmolded plastic) to define electrodes on either side of jaw liner 184 on the blade facing side of jaw member 164. The electrically conductive surfaces 188, in such aspects, are connected to generator 200 (FIG. 1) and may be energized for use in bipolar and/or monopolar configurations, e.g., energized to the same potential as one another and/or blade 162 and/or different potentials as one another and/or blade 162. In aspects, electrically conductive surfaces 188 are disposed at additional or alternative locations on jaw member 164, e.g., along either or both sides thereof, along a back surface thereof, etc.

Again referring to FIGS. 4-6, jaw liner 184 is shaped complementary to a cavity 185 defined within structural body 182, e.g., defining a T-shaped configuration, to facilitate receipt and retention therein, although other configurations are also contemplated. Jaw liner 184 is fabricated from an electrically insulative, compliant material such as, for example, polytetrafluoroethylene (PTFE). The compliance of jaw liner 184 enables blade 162 to vibrate while in contact with jaw liner 184 without damaging components of ultrasonic surgical instrument 100 (FIG. 1) and without compromising the hold on tissue clamped between jaw member 164 and blade 162. Jaw liner 184 extends from structural body 182 towards blade 162 to inhibit contact between structural body 182 and blade 162 in the approximated position of jaw member 164. The insulation of jaw liner 184 maintains electrical isolation between blade 162 and structural body 182 of jaw member 164, thereby inhibiting shorting.

Figure 7:
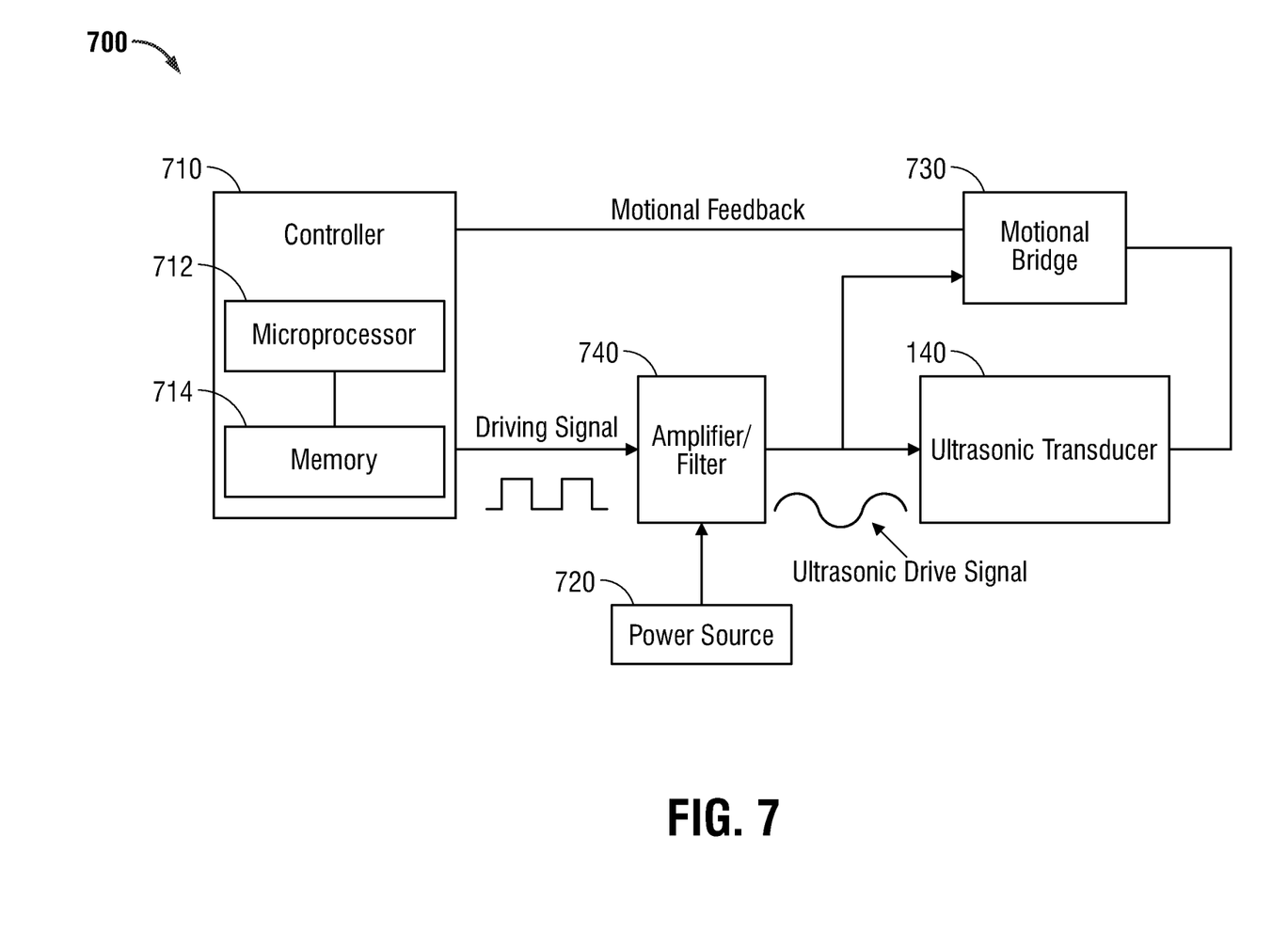
FIG. 7 is a block diagram of an ultrasonic control system configured for use in accordance with the present disclosure.

Turning to FIG. 7, an ultrasonic control system 700 of surgical instrument 100 of surgical system 10 (FIG. 1) is detailed, although the aspects and features of ultrasonic control system 700 may similarly apply, to the extent consistent, to surgical instrument 20 (FIG. 2) and/or any other suitable surgical instrument or system, whether an ultrasonic-only instrument or system or a multi-modality surgical instrument or system (e.g., incorporating ultrasonic and electrosurgical functionality). Ultrasonic control system 700 includes a controller 710 (e.g., of generator 200 (FIG. 1), ultrasonic generator 310 (FIG. 2), or any other suitable generator) and a power source 720 (e.g., generator 200 (FIG. 1), battery 400 (FIG. 2), or any other suitable power source) configured to control and power the electrical input to the ultrasonic transducer 140. Controller 710, more specifically, includes a microprocessor 712 and memory 714, e.g., storing instructions to be executed by microprocessor 712 to control the ultrasonic drive signal provided to ultrasonic transducer 140.

Ultrasonic control system 700 further includes a motional bridge 730 configured to sense a mechanical motion, e.g., a magnitude and frequency of mechanical motion, of ultrasonic transducer 140 (although other suitable mechanical motion sensing features are also contemplated), and an amplifier/filter 740. The mechanical motion feedback provided by motional bridge 730 to controller 710 enables controller 710 to control the frequency and/or magnitude of the driving signal, e.g., the high voltage AC driving signal or pulse-width modulation duty cycle, provided to amplifier/filter 740 so that amplifier/filter 740 provides a suitable ultrasonic drive signal to ultrasonic transducer 140 to achieve a target amount of mechanical motion of ultrasonic transducer 140 at its resonance frequency (or dithered thereabout). Controller 710 is also configured to monitor the resonant frequency of ultrasonic transducer 140, which varies throughout use such as, for example, due to changes in load applied to blade 162 (FIG. 4), temperature of blade 162 (FIG. 4), and/or other factors.

In aspects, and with additional reference to FIG. 4, ultrasonic control system 700 may perform a dithering control of the driving signal supplied to the ultrasonic transducer 140 to thereby control a velocity of the blade 162, where the velocity of the blade 162 is based upon the mechanical motion produced by the ultrasonic transducer 140 and, thus, the frequency and magnitude of the driving signal supplied to the ultrasonic transducer 140. The velocity of the blade 162, and/or the corresponding mechanical motion of ultrasonic transducer 140 that produces the velocity, is calculated by the mechanical motion feedback from motional bridge 730 to controller 710. The velocity at the resonant frequency of ultrasonic transducer 140 is at a maximum for the given magnitude of the ultrasonic drive signal supplied to the ultrasonic transducer 140. For example, when ultrasonic transducer 140 vibrates to produce a mechanical motion at the resonant frequency, thereby producing a maximum velocity of the blade 162 for that magnitude, controller 710 may maintain the current driving signal to amplifier/filter 740, thereby maintaining the velocity of blade 162. When the desired velocity of the blade 162 is below the actual velocity, controller 710 may adjust the drive signal so that the frequency of the ultrasonic drive signal varies from the resonant frequency, while maintaining the magnitude of the ultrasonic drive signal, thereby decreasing the mechanical motion produced by the ultrasonic transducer 140 and decreasing the velocity of the blade 162. Increasing or decreasing the velocity of the blade 162 increases or decreases, respectively, the rate of change in temperature, e.g., the heating, of tissue in contact with the blade 162; thus, modifying the velocity of the blade 162 may be utilized to control tissue treatment to achieve a desired tissue treatment outcome, e.g., tissue sealing or tissue transection. The upper and lower bounds of the frequency variability range may be based on the negative three dB point of the frequency bandwidth centered at the resonant frequency, although other configurations are also contemplated. While sacrificing the energy delivery efficiency, the dithering control can smoothly change the velocity of the blade 162 without the need to modify the magnitude of the drive signal or to stop the drive signal to the ultrasonic transducer 140.

Again, referring to FIG. 7, controller 710 may analyze the ultrasonic drive signal to calculate a phase difference between the ultrasonic drive signal and the motional feedback signal, and to perform a dithering control based on the phase difference. Generally, when the phase difference is zero, an in phase condition, ultrasonic transducer 140 is operating at resonance and is considered substantially resistive. Otherwise, ultrasonic transducer 140 is operating off-resonance and the electrical characteristic is considered capacitive or inductive, meaning that the energy is not optimally supplied to ultrasonic transducer 140. The dithering control based on the phase allows the phase difference to vary within a range about the zero phase difference and defined by upper and lower bounds of the phase difference.

In this regard, the dithering control may be a smooth, stepped, or pulsed function between two fixed points around the zero phase point. When the phase difference is greater than the upper bound of the phase range or less than the lower bound of the phase range, controller 710 may adjust the driving signal so that the frequency of the ultrasonic drive signal is decreased or increased, as necessary, to bring the phase difference back into the phase range.

Figure 8:
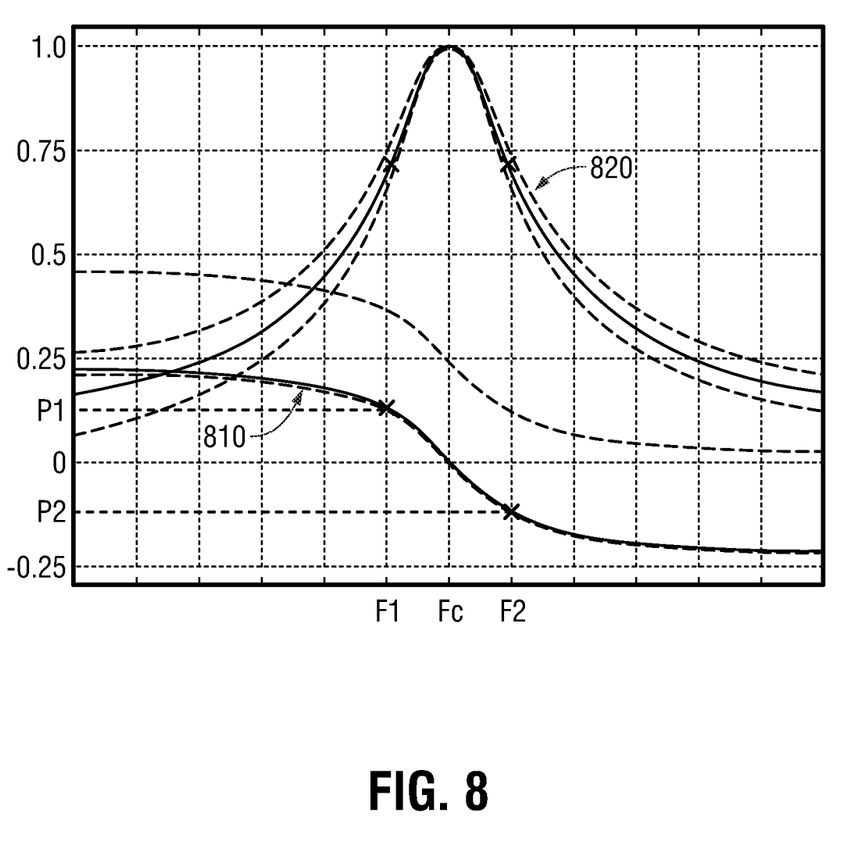
FIG. 8 is a graphical illustration of frequency and mechanical responses in accordance with the present disclosure.

With additional reference to FIG. 8, a phase curve 810 and a mechanical response curve 820 of an ultrasonic transducer are illustrated. The horizonal axis represents frequencies, and Fc represents the resonant frequency. The vertical axis represents a phase and "0" represents a zero phase. The intersection point between phase curve 810 and the zero phase line corresponds to the resonant frequency Fc in the horizontal axis. At the resonant frequency Fc, which corresponds to zero phase in the vertical axis, the amplitude of mechanical response curve 820 reaches the maximum. In other words, at the resonant frequency Fc, the velocity of the blade 162 (FIG. 4) is maximized since the ultrasonic transducer 140 is substantially resistive and, thus, most of the energy is transmitted to the blade 162 (FIG. 4) for treating tissue. On the other hand, when the frequency of the ultrasonic transducer 140 is not at the resonant frequency Fc, the electric load presented by the ultrasonic transducer 140 is not substantially resistive but is reactive. Thus, a portion of the provided energy is lost due to inefficiency; that is, the efficiency of the energy transfer to the blade 162 (FIG. 4), in the form of blade velocity, drops. Hence, tracking at or around the resonant frequency is a way to increase energy transfer efficiency. In a case when the frequency of the ultrasonic transducer 140, for example, is lower than F1, which is the lower bound of the frequency range, ultrasonic control system 700 may adjust the driving signal to increase the frequency of the ultrasonic drive signal to be supplied to the ultrasonic transducer 140 and if the frequency is, for example, greater than F2, which is the upper bound of the frequency range, ultrasonic control system 700 may adjust the driving signal to decrease the frequency of the ultrasonic drive signal.

More specifically, according to aspects of the present disclosure, ultrasonic control system 700 may perform the frequency dithering control around the resonant frequency Fc and within a particular frequency range to control the velocity of the blade 162 (FIG. 4), meaning that ultrasonic control system 700 does not stop supply of the energy (or vary the magnitude thereof) even if the velocity of the blade 162 (FIG. 4) is greater than the resonant frequency Fc. Rather, a range of frequencies around the resonant frequency Fc may be selected or set so that ultrasonic control system 700 achieves a desired velocity of the blade 162 (FIG. 4) while the frequency falls within the frequency range. For example, the frequency range may be from frequency F1 to frequency F2. For a relatively narrow range, e.g., the closer the frequency is maintained to the resonant frequency Fc, the velocity of the blade 162 (FIG. 4) approaches its maximum. The broader the range, the farther the frequency is permitted to stray from the resonant frequency Fc, the lower the velocity of the blade 162 (FIG. 4). The velocity of the blade 162 (FIG. 4) may be considered an average velocity, as the actual velocity may be different at any given point based on the operating frequency at that point. For example, where the maximum (resonant) blade velocity is 10 m/s and the frequency is permitted to vary to produce a minimum blade velocity of 5 m/s, the average blade velocity (or the blade velocity as a result of the dithering) may be considered 7.5 m/s.

In aspects, the difference between F1 and Fc may be different from the difference between Fc and F2. For example, F1 may be farther away from Fc than F2, or F2 may be farther away from Fc than F1. Alternatively, F1 and F2 are equally distant from Fc or are at negative three dB points with respect to the resonant frequency Fc. As the resonant frequency Fc of ultrasonic transducer 140 changes due to changes in the load applied to blade 162 (FIG. 4), temperature of blade 162 (FIG. 4), and/or other factors, the lower and upper frequencies F1 and F2 may correspondingly change. Alternatively or additionally, the lower and upper frequencies F1 and F2 may be predetermined to cover the change in the resonant frequency. In other words, a potential range, where the resonant frequency of ultrasonic transducer 140 falls, is included within the lower and upper frequencies F1 and F2. In this case, the lower and upper frequencies F1 and F2 of the range may not change according to the change in the resonant frequency.

In aspects, ultrasonic control system 700 may perform a dithering control based on a phase, as controlling the phase difference to zero achieves resonance. In particular, the phase is calculated from a phase difference between the ultrasonic drive signal provided to ultrasonic transducer 140 and the motional feedback signal indicative of mechanical motion output by the ultrasonic transducer 140. The zero phase point corresponds to the resonant frequency Fc in FIG. 8. The range of phases may be from the lower bound phase P2, which corresponds to the upper frequency F2 of the frequency range, to the upper bound phase P1, which corresponds to the lower bound frequency F1 of the frequency range. When the phase is within the range from P1 to P2, ultrasonic control system 700 may maintain the frequency of the ultrasonic drive signal. When the phase is outside of the phase range, ultrasonic control system 700 may modify the ultrasonic drive signal to return to a phase difference within the phase range. In an aspect, the magnitude of the ultrasonic drive signal is maintained during the phase (and/or frequency) dithering control.

Figure 9:
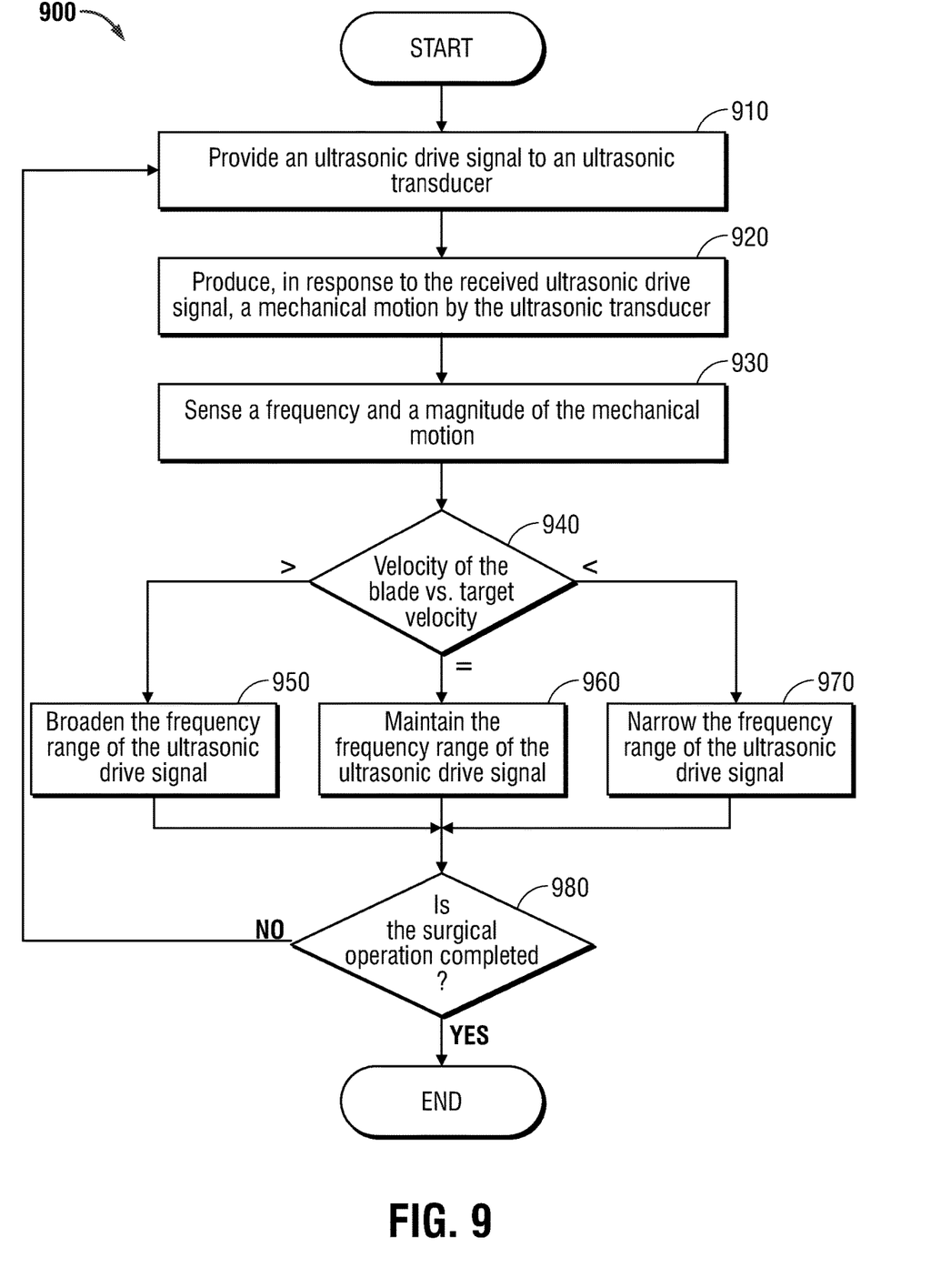
FIG. 9 is a flowchart illustrating a method for frequency dithering in accordance with the present disclosure.

Turning to FIG. 9, a method for performing a frequency dithering control for an ultrasonic surgical instrument is shown generally as a method 900. Method 900 may be implemented using surgical system 10 (FIG. 1) (e.g., ultrasonic control system 700 (FIG. 7)), surgical instrument 20 (FIG. 2), and/or any other suitable surgical instrument or system. Method 900, as described below, controls a level of energy output from the ultrasonic transducer and, thus, a velocity of the blade coupled thereto not based on the magnitude or on/off control of the ultrasonic drive signal, but based on a range of frequencies (the frequency range), thereby reducing or removing transients between on and off stages of supplying the ultrasonic drive signals. The frequency range includes the resonant frequency of the ultrasonic transducer. The frequency range may be dynamically changing or shifting to account for varying resonant frequencies during a surgical operation due to changes in load applied to blade 162 (FIG. 4), temperature of blade 162 (FIG. 4), and/or other factors, or may be constant. The size of the frequency range determines the resultant velocity (or average) velocity of the blade. Alternatively or additionally, method 900 may employ a velocity or phase range of ultrasonic transducer 140 instead of the frequency range. Detailed descriptions for phase dithering and velocity dithering controls are omitted because persona being skilled in the art would readily apprehend based on the present disclosure.

Method 900 begins at step 910, where an ultrasonic generator provides an ultrasonic drive signal to an ultrasonic transducer. In particular, a controller (e.g., controller 710 (FIG. 7) of ultrasonic system) supplies the ultrasonic drive signal by using the power from a power supply. The drive signal has a frequency that varies within a frequency range.

At step 920, in response to the received ultrasonic drive signal, the ultrasonic transducer produces a mechanical motion. A motional bridge, such as motional bridge 730 (FIG. 7), senses the mechanical motion at step 930. The motional bridge may further sense the frequency of the mechanical motion, which corresponds to the resonant frequency, and the magnitude of the mechanical motion. Mechanical motion and/or the resonant frequency may be sensed in any other suitable manner. The mechanical motion produces a velocity of the blade coupled to the ultrasonic transducer, which may be calculated based on the mechanical motion output and other factors, as understood by a person skilled in the art.

At step 940, it is determined whether the velocity of the blade is equal to, greater than, or less than a target velocity (the target velocity may be determined for example, based upon the activated state, e.g., the LOW power state may provide a first target velocity (for example, 10 m/s) and the HIGH power state may provide a second, greater target velocity (for example 7 m/s)). It is noted that the target velocity need not be a static value but may change over time and/or in response to sensed conditions such as, for example, in accordance with a tissue sealing algorithm or tissue cutting algorithm implemented by the generator.

The initial frequency range within which the frequency of the drive signal varies may be determined prior to or during the surgical operation. To pre-determine the frequency range, the controller may provide a test signal to the ultrasonic transducer and analyze a response from the ultrasonic transducer. The test signal may be an impulse signal or have a saw-tooth, sinusoid, step, or other shape readily apprehended by persons having ordinary skilled in the art. The response signal (e.g., an impulse response) may have characteristics of the ultrasonic transducer, such as a resonant frequency of, a level of mechanical wear of, and/or a system ID of the ultrasonic transducer. When the resonant frequency of the ultrasonic transducer is measured during the surgical operation, the frequency range may be reset during the surgical operation.

When it is determined that the blade velocity is greater than the target velocity at step 940, the controller may broaden the frequency range within which the ultrasonic drive signal is permitted to operate at step 950, thereby decreasing the (average) velocity of the blade towards or to the target velocity. When it is determined that the velocity of the blade is equal to (or sufficiently close, e.g., within 10% of) the target velocity at step 940, the controller may maintain the frequency range of the ultrasonic drive signal at step 960. When it is determined that the blade velocity is less than the target velocity at step 940, the controller may narrow the frequency range of the ultrasonic drive signal at step 970, thereby increasing the (average) velocity of the blade towards or to the target velocity. In an aspect, the magnitude of the ultrasonic drive signal may be maintained during steps 950-970.

After the steps 950-970, it is also determined whether the surgical operation is completed at step 980. Until the surgical operation is completed, steps 910-980 are repeated, and when the surgical operation is completed, method 900 is ended. For example, some or all of steps 910-980 may repeat throughout different portions of a tissue-sealing and/or cutting algorithm and/or when the target velocity changes.

In aspects, for example, assuming for explanation purpose only that the velocity of blade 162 (FIG. 4) is 10 m/s at the resonant frequency, the velocity of the blade 162 (FIG. 4), which corresponds to the lower or upper bound of the frequency range, can be 5 m/s, and thus, the average velocity is 7.5 m/s. When the lower or upper bound of the frequency range is farther away from the resonant frequency, the average velocity can be lower than 7.5 m/s. With this consideration, the average velocity of blade 162 (FIG. 4) can be controlled by selecting a different frequency range, as detailed above.

While several aspects of the disclosure have been detailed above and are shown in the drawings, it is not intended that the disclosure be limited thereto, as it is intended that the disclosure be as broad in scope as the art will allow and that the specification be read likewise. Therefore, the above description and accompanying drawings should not be construed as limiting, but merely as exemplifications of particular aspects. Those skilled in the art will envision other modifications within the scope and spirit of the claims appended hereto.

What is claimed is:

1. An ultrasonic surgical system comprising:
    an ultrasonic generator configured to provide an ultrasonic drive signal;
    an ultrasonic transducer electrically coupled to the ultrasonic generator to receive the ultrasonic drive signal therefrom and configured, in response to the received ultrasonic drive signal, to produce a mechanical motion;
    a sensor configured to sense a frequency and a magnitude of the mechanical motion; and
    a controller configured to:
        receive a target mechanical motion to be produced by the ultrasonic transducer and control the ultrasonic drive signal so that a frequency of the ultrasonic drive signal falls within a frequency range around a resonant frequency of the ultrasonic transducer, the frequency range corresponding to the target mechanical motion produced by the ultrasonic transducer; and
        at least one of:
            increase the frequency range of the ultrasonic drive signal when the mechanical motion is greater than the target mechanical motion; or
            decrease the frequency range of the ultrasonic drive signal when the mechanical motion is less than the target mechanical motion.

2. The ultrasonic surgical system according to claim 1, wherein the controller is further configured to provide a test signal to the ultrasonic transducer.

3. The ultrasonic surgical system according to claim 2, wherein the test signal is an impulse signal.

4. The ultrasonic surgical system according to claim 2, wherein the controller is further configured to analyze an impulse response from the ultrasonic transducer in response to the test signal.

5. The ultrasonic surgical system according to claim 4, wherein the resonant frequency of the ultrasonic transducer is calculated based on the impulse response.

6. The ultrasonic surgical system according to claim 1, wherein the controller is further configured to maintain the frequency range of the ultrasonic drive signal when the mechanical motion is equal to the target mechanical motion.

7. The ultrasonic surgical system according to claim 1, wherein the sensor is a motional bridge.

8. The ultrasonic surgical system according to claim 1, wherein an upper bound and a lower bound of the frequency range are −3 dB points with respect to the resonant frequency.

9. A control method for controlling ultrasonic drive signal to produce mechanical ultrasonic energy, the control method comprising:
    providing, by an ultrasonic generator, an ultrasonic drive signal to an ultrasonic transducer;
    in response to the received ultrasonic drive signal, producing a mechanical motion by the ultrasonic transducer;
    sensing a frequency and a magnitude of the mechanical motion;
    receiving a target mechanical motion to be produced by the ultrasonic transducer;
    controlling the ultrasonic drive signal so that a frequency of the ultrasonic drive signal falls within a frequency range around a resonant frequency of the ultrasonic transducer, the frequency range corresponding to the target mechanical motion produced by the ultrasonic transducer; and
    at least one of:
        increasing the frequency range of the ultrasonic drive signal when the mechanical motion is greater than the target mechanical motion, or
        decreasing the frequency range of the ultrasonic drive signal when the mechanical motion is less than the target mechanical motion.

10. The control method according to claim 9, further comprising:
    providing a test signal to the ultrasonic transducer.

11. The control method according to claim 10, wherein the test signal is an impulse signal.

12. The control method according to claim 10, further comprising:
    analyzing an impulse response from the ultrasonic transducer in response to the test signal.

13. The control method according to claim 12, further comprising:
    calculating the resonant frequency of the ultrasonic transducer based on the impulse response.

14. The control method according to claim 9, wherein controlling the ultrasonic drive signal includes:
    maintaining the frequency range of the ultrasonic drive signal when the mechanical motion is equal to the target mechanical motion.

15. The control method according to claim 9, controlling the ultrasonic drive signal includes:
    regulating a phase different between the ultrasonic drive signal and a motional feedback signal to be within a predetermined phase range.

16. A nontransitory computer-readable medium including processor-executable instructions that, when executed by a processor, are configured to cause a computer to perform a method for controlling ultrasonic drive signal to produce mechanical ultrasonic energy, the method for controlling ultrasonic drive signal comprising:
    providing, by an ultrasonic generator, an ultrasonic drive signal to an ultrasonic transducer;
    in response to the received ultrasonic drive signal, producing a mechanical motion by the ultrasonic transducer;
    sensing a frequency and a magnitude of the mechanical motion;
    receiving a target mechanical motion to be produced by the ultrasonic transducer; and controlling the ultrasonic drive signal so that a frequency of the ultrasonic drive signal falls within a frequency range around a resonant frequency of the ultrasonic transducer, the frequency range corresponding to the target mechanical motion produced by the ultrasonic transducer; and at least one of:
  increasing the frequency range of the ultrasonic drive signal when the mechanical motion is greater than the target mechanical motion, or
  decreasing the frequency range of the ultrasonic drive signal when the mechanical motion is less than the target mechanical motion.

\* \* \* \* \*